United States Patent [19]

Goto et al.

[11] 4,088,702
[45] May 9, 1978

[54] PROCESS FOR PREPARING O-PHENYLPHENOL

[75] Inventors: Hideo Goto; Nobuyori Shibamoto; Shunsaku Tanaka, all of Wakayama, Japan

[73] Assignee: Sugai Chemical Industry Company Limited, Wakayama, Japan

[21] Appl. No.: 683,054

[22] Filed: May 4, 1976

[30] Foreign Application Priority Data

May 14, 1975 Japan .................................. 50-57806
Jun. 23, 1975 Japan .................................. 50-77773

[51] Int. Cl.² ............................................. C07C 37/06
[52] U.S. Cl. ..................................... 568/747; 252/439
[58] Field of Search ......................................... 260/620

[56] References Cited

U.S. PATENT DOCUMENTS

| | | | |
|---|---|---|---|
| 3,580,970 | 5/1971 | Swift | 260/620 |
| 3,697,606 | 10/1972 | Freindwald et al. | 260/620 |
| 3,923,695 | 12/1975 | Weissel et al. | 260/620 |
| 3,932,536 | 1/1976 | Weissel et al. | 260/620 |
| 3,933,924 | 1/1976 | Weissel et al. | 260/620 |
| 3,972,951 | 8/1976 | Kapnes et al. | 260/620 |
| 3,980,716 | 9/1976 | Elliot | 260/620 |

*Primary Examiner*—Norman Morgenstern
*Attorney, Agent, or Firm*—Larson, Taylor and Hinds

[57] ABSTRACT

A process for preparing o-phenylphenol by dehydrogenating at least one of cyclohexanone dimer and o-cyclohexylphenol in the presence of a catalyst, characterized in that the catalyst is one prepared by causing a metal oxide carrier to support at least one compound substantially producing platinum or palladium on the resulting catalyst, at least one compound substantially producing an alkali metal oxide on the resulting catalyst and at least one of hydrogen sulfide, organic sulfur compound and alkali metal sulfide, and heating the carrier at 300° to 400° C.

8 Claims, No Drawings

PROCESS FOR PREPARING O-PHENYLPHENOL

This invention relates to a process for preparing o-phenylphenol, and more particularly to a process for preparing o-phenylphenol by dehydrogenating cyclohexanone dimer or o-cyclohexylphenol.

O-Phenylphenol was produced chiefly as a by-product of the alkali hydrolysis of chlorobenzene for the synthesis of phenol. With the progress of petrochemistry, however, the cumene process has taken over the above-mentioned process, consequently reducing the supply of o-phenylphenol as the by-product despite the increasing demand for the compound for use in surfactants and disinfectants and giving rise to the necessity to develop a process for the production of o-phenylphenol per se in order to compensate for the reduction in the supply of the by-product. Accordingly processes for producing o-phenylphenol have been developed in which cyclohexanone dimer or o-cyclohexylphenol is catalytically dehydrogenated. They are grouped into three types. Publicly Disclosed Japanese Patent Publication No. 11823/1972 discloses one type of the processes which uses a catalyst containing copper, nickel, aluminum and chromium and at least one of alkali sulfates and alkali carbonates. The process of another type which is disclosed in Publicly Disclosed Japanese Patent Publication No. 35365/1974 uses a catalyst comprising a carrier such as alumina or activated carbon having a relatively large surface area and a small amount of palladium or platinum adsorbed by the carrier. Publicly Disclosed Japanese Patent Publication No. 72240/1974 discloses a process of the third type which uses a catalyst comprising an alumina or silica-alumina carrier and specified amounts of platinum and a hydroxide, oxide or carbonate of sodium or potassium. However, these processes have the following drawbacks. The first-mentioned process is industrially very disadvantageous in that it requires evaporation and purification steps because of the low selectivity in giving o-phenylphenol. When palladium is used in the process of the second type, problems are encountered in the thermal stability and toxicity of the catalyst and it is extremely difficult to maintain a high selectivity for a prolonged period of time. Furthermore when platinum is used in this process, the life of the catalyst is relatively short while the selectivity for o-phenylphenol is not fully satisfactory. Being more excellent in the life of the catalyst than the process using platinum and/or palladium, the process of the third type is not sufficient and likely to give dibenzofuran, biphenyl or like by-product.

An object of this invention is to provide a process for preparing o-phenylphenol with a high selectivity.

Another object of this invention is to provide a process for preparing o-phenylphenol with a catalyst which is serviceable for a prolonged period of time, or in other words, to provide a catalyst having a prolonged life for use in the production of o-phenylphenol.

Still another object of this invention is to provide a process for preparing o-phenylphenol with the formation of by-product greatly reduced.

These and other objects of this invention will become apparent from the following description.

In preparing o-phenylphenol by dehydrogenating at least one of cyclohexanone dimer and o-cyclohexylphenol in the presence of a catalyst, the objects of this invention can be fulfilled by the use of a catalyst which is prepared by causing a metal oxide carrier to support at least one compound substantially producing platinum or palladium on the resulting catalyst, at least one compound substantially producing an alkali metal oxide on the resulting catalyst and at least one of hydrogen sulfide, organic sulfur compound and alkali metal sulfide, and heating the carrier at 300° to 400° C.

In preparing o-phenylphenol by dehydrogenating at least one of cyclohexanone dimer and o-cyclohexylphenol, our research has revealed that when the dehydrogenation is conducted in the presence of a catalyst which is prepared by causing a metal oxide carrier to support at least one compound substantially producing platinum or palladium on the resulting catalyst, at least one compound substantially producing an alkali metal oxide on the resulting catalyst and at least one of hydrogen sulfide, organic sulfur compound and alkali metal sulfide, and heating the carrier at 300° to 400° C, the catalyst exhibits a higher selectivity with a longer life than the catalysts described above while greatly reducing the formation of by-product. We have also found that when the catalyst does not contain an alkali metal oxide, the above improved effects greatly reduce. Based on these novel findings, this invention has been accomplished.

The catalysts to be used in this invention are novel catalysts which have not been used for the production of o-phenylphenol. The catalyst is one prepared by causing a metal oxide carrier to support at least one compound substantially producing platinum or palladium on the resulting catalyst, at least one compound substantially producing an alkali metal oxide on the resulting catalyst and at least one of hydrogen sulfide, organic sulfur compound and alkali metal sulfide, and heating the carrier at 300° to 400° C. The useful metal oxide carrier include those heretofore used such as silica, alumina, magnesia, calcium oxide, etc. Preferable examples are alumina, silica, alumina-silica and alumina-magnesia, and γ-alumina is especially preferable. The specific surface area of the metal oxide carrier to be used is usually 100 to 300 m$^2$/g, preferably about 150 to about 250 m$^2$/g (as determined by BET method). The carrier may have any of suitable forms such as pellets, particles, granules, etc.

The platinum and/or palladium may be so supported by the carrier that they act as such elements when used substantially in the form of a catalyst. The amount of platinum and/or palladium to be used is 0.1 to 3.0% by weight, preferably about 0.3 to about 1.0% by weight, based on the carrier. With extremely lesser amounts, low catalytic activity results, whereas amounts above 3.0% by weight will not give improved results.

The compounds (hereinafter referred to as "alkali substance") substantially producing an alkali metal oxide on the resulting catalyst to be used in this invention are a wide variety of compounds which produce alkali metal oxides by being baked at 300° to 400° C. Examples are hydroxide, carbonate and the like of alkali metals which are preferably sodium and potassium. The amount of the alkali substance to be supported by the carrier is 0.5 to 8.0% by weight, preferably 1 to 7% by weight. According to this invention it is critical to use such alkali substance; when the alkali substance is not used even if the foregoing sulfur compounds are used, the resulting catalyst gives very poor results in improving selectivity and service life.

The organic sulfur compounds useful in this invention include carbon disulfide, aliphatic mercaptans, aromatic mercaptans, heterocyclic compounds, monosulfides represented by the formula R—S—R' wherein R and R' may be the same or different and are each aliphatic alkyl or benzyl or phenyl group having or not having alkyl, disulfides represented by the formula R—S—S—R' wherein R and R' are as defined above, etc. More specific examples are methyl mercaptan, ethyl mercaptan, lauryl mercaptan, and like aliphatic mercaptans, phenyl mercaptan, benzyl mercaptan, and like aromatic mercaptans, thiophene, thiophthene, thionaphthene, thiazole, thiane and like heterocyclic compounds, dimethyl sulfide, diethyl sulfide, divinyl sulfide, diphenyl sulfide, ethylmethyl sulfide, p-phenylmethyl sulfide and like monosulfides, dimethyl disulfide, diethyl disulfide, dipropyl disulfide, diphenyl disulfide, ethylmethyl disulfide, etc. Preferable among these examples are methyl mercaptan, ethyl mercaptan, lauryl mercaptan, phenyl mercaptan, thiophene, thiophthene, dimethyl sulfide, diethyl sulfide, dimethyl disulfide, etc.

The alkali metal sulfides usable in this invention include, for example, sodium sulfide, potassium sulfide, rubidium sulfide, cesium sulfide and lithium sulfide, among which sodium sulfide, potassium sulfide, rubidium sulfide and cesium sulfide are preferable.

According to this invention, hydrogen sulfide, organic sulfur compounds and alkali metal sulfides may be used singly, or at least two of them are conjointly usable. Although the amount of such sulfur compound to be used is suitably determined in accordance with the kind of the compound and the amounts of alkali and platinum and/or palladium supported by the carrier, it is usually up to 5% by weight, preferably about 0.05 to about 2.0% by weight, based on the total amount of alkali substance and platinum and/or palladium used.

According to this invention, the carrier can be made to support one or at least two of alkali metal salts of sulfur-oxygen acids when so required. The alkali metal salts of sulfur-oxygen acids useful in this invention are versatile; examples are alkali metal salts and alkali metal hydrogen salts of sulfuric acid, sulfurous acid and thiosulfuric acid. More specific examples are sodium sulfate, potassium sulfate, rubidium sulfate, cesium sulfate and like alkali sulfates; sodium thiosulfate, potassium thiosulfate and like alkali thiosulfates; sodium sulfite, potassium sulfite and like alkali sulfites; sodium bisulfate, potassium bisulfate and like alkali bisulfates; and sodium bisulfite, potassium bisulfite and like alkali bisulfites. Preferable among these examples are sodium sulfate, potassium sulfate, rubidium sulfate, cesium sulfate, sodium thiosulfate, sodium bisulfite, potassium bisulfite, potassium thiosulfate, etc. The amount of the sulfur-oxygen acid salt to be supported by the carrier is about 0.1 to about 10% by weight, preferably about 2.0 to about 5.0% by weight, based on the carrier. However, when an alkali metal sulfate is used as the alkali metal salt of sulfur-oxygen acid in this invention, the sulfate must be used conjointly with hydrogen sulfide and/or organic sulfur compound.

According to this invention, the metal oxide carrier may be made to support the alkali substance, at least one of platinum and palladium, at least one of hydrogen sulfide, organic sulfur compound and alkali metal sulfide, and further when required, sulfur-oxygen acid salt by any method, insofar as the desired amounts of the effective components can be supported by the carrier. Any one of these effective components may be supported prior to support of the other components, or they may be supported at the same time. Preferably, however, platinum and/or palladium may be supported first, then the alkali substance and finally at least one of hydrogen sulfide, organic sulfur compound and alkali metal sulfide. Typically platinum and/or palladium can be supported by the carrier by the steps of immersing a suitably shaped product of metal oxide carrier in an aqueous solution of water-soluble platinum compound and/or palladium compound, drying the carrier, heating the carrier in nitrogen atmosphere at about 300° to about 400° C for several hours and thereafter reducing the product with hydrogen at about 300° to about 400° C to separate out the platinum and/or palladium. Subsequently the platinum and/or palladium supporting carrier is immersed in an aqueous solution of alkali substance and baked in the same manner as above. Finally the resulting carrier is caused to support at least one of hydrogen sulfide, organic sulfur compound and alkali metal sulfide (hereinafter referred to generally as "sulfur-containing compound"). For this purpose, for example, the carrier may be contacted with the sulfur-containing compound itself or with a mixture thereof and an inert gas, when the compound is a gas (at room temperature). If the sulfur-containing compound is a liquid (at room temperature), the carrier is immersed in the compound itself or an aqueous solution thereof or is otherwise impregnated with the compound or with its aqueous solution. Further if the sulfur-containing compound is a solid, the carrier is immersed in an aqueous solution or dispersion thereof. Subsequently the resulting carrier is dried and thereafter heated in the same manner as above at 300° to 400° C.

With this invention, such sulfur-containing compound needs only to be supported on the metal oxide carrier substantially during reaction. Thus when cyclohexanone dimer and/or o-cyclohexylphenol is actually dehydrogenated, the sulfur-containing compound can be charged along with the starting material in the initial stage of the reaction, When dehydrogenating at least one of cyclohexanone dimer and o-cyclohexylphenol with the novel catalyst described, either a vapor-phase method or a liquid-phase method can be adopted. However, the vapor-phase method is preferable in view of the ease of reaction procedure and reaction efficiency. The vapor-phase reaction can be effected, for example, by vaporizing the dimer of cyclohexanone and/or o-cyclohexylphenol as by a pre-heater and feeding the resulting vapor, as it is or as diluted with an inert gas, to a reactor packed with the catalyst. The feed rate of the starting material may be suitably determined in accordance with the reaction temperature and the kind of the catalyst. Material calculated as a liquid at room temperature is fed at a rate of usually 0.1 to 1.5 times, preferably 0.2 to 0.7 time, the volume of the catalyst per hour. The reaction temperature also varies with the kind of the catalyst and the feed rate of the material and is usually about 250° to about 420° C, preferably about 300° to about 400° C.

The catalysts of this invention can be regenerated effectively by usual methods, for example, by oxidizing the catalyst with air or a mixture of air and nitrogen gas at about 300° to about 400° C and thereafter reducing the catalyst with hydrogen at about 300° to about 350° C. When the catalysts containing hydrogen sulfide and/or organic sulfur compound is regenerated, the catalyst needs the same treatment that hydrogen sulfide and/or organic sulfur compound is supported on the carrier. The catalyst thus regenerated is almost as active as a fresh catalyst.

This invention will be described below in detail with reference to examples.

EXAMPLE 1

γ-Alumina pellets (75 g) having a specific surface area of 190 to 230 m$^2$/g, diameter of 2.9 mm and thickness of 3.0 mm are uniformly impregnated with an aqueous solution prepared by dissolving 1g of chloroplatinic acid hexahydrate in 200 ml of 0.3% aqueous solution of hydrochloric acid and are then dried. The pellets are placed in a tube, heated in a nitrogen atmosphere at 350° C for 3 hours and then reduced at the same temperature for 3 hours with hydrogen introduced into the tube to cause pellets to support platinum. 50 g of the resulting mass thus treated are fully immersed in an aqueous solution of 1g of potassium hydroxide in 60 ml of deionized water, then withdrawn and heated at 350° C for 3 hours.

A 34.5 ml portion of the catalyst is packed in a heat-resistant glass reaction tube, 27 mm in inside diameter and 1,000 mm in length, and hydrogen is introduced into the tube at a rate of 290 ml/min. at 340° C while simultaneously feeding carbon disulfide in an amount of 0.1% by weight based on the weight of the catalyst. Subsequently cyclohexanone dimer starting material is fed to the tube at a rate of 15.5 ml/hr. while introducing hydrogen into the tube at a rate of 290 ml/min. and maintaining the reaction temperature at 300° to 400° C. During the reaction, the resulting product is sampled from time to time and analyzed by gas chromatography. It is found that the conversion of the cyclohexanone dimer starting material achieved is always 100% over the reaction period of 2,000 hours. The selectivity for o-phenylphenol is also measured with the result given in Table 1 below.

EXAMPLES 2 TO 4

The same procedure as in Example 1 is repeated except that in place of 0.1 wt.% of carbon disulfide, 0.4 wt.% of thiophene, 0.4 wt.% of lauryl mercaptan and 0.3 wt.% of diethyl sulfide are used in the Examples respectively. The same analysis as conducted in Example 1 confirms 100% conversion in each Example. Table 1 also shows the selectivities for o-phenylphenol.

EXAMPLES 5 AND 6

The same procedure as in Example 1 is repeated except that in place of 0.1 wt.% of carbon disulfide, 3.0 wt.% of sodium thiosulfide heptahydrate and 1.0 wt.% of sodium sulfide are used in the Examples respectively. The same analysis as conducted in Example 1 confirms 100 % conversion in each Example. Table 1 also shows the selectivities for o-phenylphenol.

EXAMPLE 7

The same procedure as in Example 1 is repeated except that in place of cyclohexanone dimer, o-cyclohexylphenol is used. During the reaction, the resulting product is sampled from time to time and analyzed by gas chromatography. It is found that the conversion of the o-cyclohexylphenol starting material achieved is always 100% over the reaction period of 1,200 hours. The selectivity for o-phenylphenol is also measured with the result given in Table 1 below.

EXAMPLE 8

The same procedure as in Example 1 is repeated except that in place of alumina pellet, alumina-magnesia pellet (alumina:magnesia = 9:1 by weight, baked product at 1,000° C for 3 hours) is used. The same analysis as conducted in Example 1 confirms 100% conversion. Table 1 also shows the selectivity for o-phenylphenol.

EXAMPLE 9

The same procedure as in Example 1 is repeated except that in place of alumina pellet, alumina-calcium oxide pellet (alumina:calcium oxide = 85:15 by weight, baked product at 600° C for 3 hours) is used. The same analysis as conducted in Example 1 confirms 100% conversion. Table 1 also shows the selectivity for o-phenylphenol.

EXAMPLE 10

The same procedure as in Example 1 is repeated except that 2.5 g of potassium bisulfite is further supported and in place of alumina pellet, alumina-silica pellet (alumina:silica = 90:10, baked product at 800° C for 3 hours) is used.

The same analysis as conducted in Example 1 confirms 100% conversion. Table 1 also shows the selectivity for o-phenylphenol.

EXAMPLE 11

The same procedure as in Example 1 is repeated except that in place of 0.1 wt.% of carbon disulfide, 0.4 wt.% of phenyl mercaptan is used.

The same analysis as conducted in Example 1 confirms 100% conversion. Table 1 also shows the selectivity for o-phenylphenol.

EXAMPLE 12

The same procedure as in Example 1 is repeated except that in place of potassium hydroxide and carbon disulfide, sodium hydroxide and dimethylsulfide are used respectively.

The same analysis as conducted in Example 1 confirms 100% conversion. Table 1 also shows the selectivity for o-phenylphenol.

EXAMPLE 13

The same procedure as in Example 1 is repeated except that in place of chloroplatininc acid hexahydrate, a mixture of chloroplatinic acid hydrate and chloropalladium (90:10 in weight ratio) is used. The same analysis as conducted in Example 1 confirms 100% conversion. Table 1 also shows the selectivity for o-phenylphenol.

COMPARISON EXAMPLE 1

The same procedure as in Example 1 is repeated except that carbon disulfide is not used. During the reaction, the resulting product is sampled from time to time and analyzed by gas chromatography. It is found that however, the conversion of cyclohexanone dimer starting material is always 100% over the reaction period of 500 hours, the above conversion lowers to 99% and 95% respectively after the reaction period of 1,200 hours and 2,000 hours are passed respectively.

Table 1

| Reaction period (hr) | Selectivity for o-phenylphenol (mol %) | | | | | | | | | | | | | Comp. Example 1 |
|---|---|---|---|---|---|---|---|---|---|---|---|---|---|---|
| | Example | | | | | | | | | | | | | |
| | 1 | 2 | 3 | 4 | 5 | 6 | 7 | 8 | 9 | 10 | 11 | 12 | 13 | |
| 1 | 95.2 | 94.1 | 91.5 | 94.1 | — | — | — | 96.7 | — | — | 94.7 | 94.0 | 93.8 | — |
| 2 | — | — | — | — | — | — | 94.5 | — | — | — | — | — | — | — |
| 3 | — | — | — | — | — | — | — | — | — | 89.1 | — | — | — | 74.0 |
| 4 | 94.1 | — | — | — | — | — | — | — | 86.2 | — | — | — | — | — |
| 5 | — | 93.4 | 91.5 | 93.2 | 93.7 | 92.7 | 94.1 | 96.0 | — | — | 94.2 | 93.3 | 93.6 | 76.3 |
| 6 | — | — | — | — | — | — | — | — | 90.5 | 91.3 | — | — | — | 78.4 |
| 7 | 94.1 | — | — | — | — | — | — | — | — | — | 94.1 | — | — | — |
| 8 | — | — | 91.0 | — | — | — | — | — | — | — | — | — | — | — |
| 9 | — | 94.2 | — | 93.8 | — | — | — | 95.9 | — | — | — | — | — | — |
| 10 | — | — | 92.2 | — | 94.4 | 93.0 | 93.2 | — | — | — | — | 93.3 | 93.5 | — |
| 11 | — | — | — | — | — | — | — | — | — | 93.4 | — | — | — | — |
| 12 | — | 93.2 | — | 93.0 | — | — | — | — | 93.0 | — | — | 93.2 | — | — |
| 20 | 94.0 | — | — | — | — | — | — | 95.7 | 95.0 | — | 93.2 | — | 93.1 | 80.0 |
| 50 | 94.0 | — | — | — | 92.8 | 92.8 | — | — | — | 93.4 | 93.8 | — | 92.9 | 85.7 |
| 100 | 93.5 | 93.0 | 93.0 | 93.0 | 92.8 | — | 93.0 | 95.7 | 94.6 | 93.1 | 93.2 | 93.0 | 92.6 | 90.5 |
| 500 | 92.5 | 93.0 | 92.8 | 92.8 | 92.3 | 92.0 | 92.5 | 95.0 | 94.2 | 92.9 | 92.3 | 92.7 | 92.3 | 94.0 |
| 1200 | 92.5 | 92.5 | 92.0 | 92.0 | 91.5 | 91.0 | 92.0 | 94.2 | 93.8 | 92.0 | 92.1 | 92.2 | 91.7 | 90.0 |
| 2000 | 92.0 | 91.0 | 90.0 | 91.2 | 90.4 | 90.2 | 90.3 | — | 92.0 | 90.9 | 91.3 | 91.7 | — | 80.0 |

EXAMPLE 14

γ-Alumina pellets (75 g) having a specific surface area of 190 to 230 m²/g, diameter of 2.9 mm and thickness of 3.0 mm are immersed in an aqueous solution containing 1g of chloroplatininc acid hexahydrate and 200 ml of hydrochloric acid having a concentration of 0.3% for full impregnation and thereafter withdrawn and dried. The pellets are placed in a tube and heated in a nitrogen atmosphere at 350° C for 3 hours. Subsequently the pellets are reduced at the same temperature for 3 hours with hydrogen introduced into the tube to cause the pellets to support platinum. 50 g of the resulting mass is immersed in an aqueous solution containing 1g of potassium hydroxide and 60 ml of deionized water and, after having been fully impregnated with the solution, the mass is withdrawn, dried and then heated at 350° C for 3 hours. Further the resulting mass thus treated is immersed in an aqueous solution containing 2.5 g of potassium sulfate and 60 ml of deionized water and, after having been dried, the mass is heated at the same temperature for 3 hours to obtain a catalyst of the present invention.

A 34.5 ml quantity of the catalyst is packed in a heat-resistant glass reaction tube, 27 mm in inside diameter and 1,000 mm in length. A 0.1 wt.% of carbon disulfide based on the mass is fed to the tube while introducing hydrogen at a rate of 290 ml/min. maintaining the temperature at 340° C. Subsequently cyclohexanone dimer is fed to the tube at a rate of 15.5 ml/hr. while introducing hydrogen at a rate of 290 ml/min. and maintaining the reaction temperature at 300° to 400° C. During the reaction, the resulting product is sampled from time to time and analyzed by gas chromatography. It is found that the conversion of the cyclohexanone dimer starting material achieved is always 100% over the reaction period of 2,000 hours. The selectivity for o-phenylphenol is also measured with the result given in Table 2 below.

EXAMPLE 15

The same procedure as in Example 14 is repeated except that in place of 0.1 wt.% of carbon disulfide and potassium sulfate, 0.4 wt.% of thiophene and sodium sulfate are used respectively.

The same analysis as conducted in Example 14 confirms 100% conversion. Table 2 also shows the selectivity for o-phenylphenol.

EXAMPLE 16

The same procedure as in Example 14 is repeated except that in place of carbon disulfide, hydrogen sulfide is used. The same analysis as in Example 14 confirms 100% conversion. Table 2 also shows the selectivity for o-phenylphenol.

EXAMPLE 17

The same procedure as in Example 14 is repeated except that in place of 2.5 g of potassium sulfate, the mixture of 1.5g of sodium sulfate and 1.0g of rubidium sulfate is used. The same analysis as in Example 14 confirms 100% conversion. Table 2 also shows the selectivity for o-phenylphenol.

EXAMPLE 18

The same procedure as in Example 14 is repeated except that in place of γ-alumina pellets and carbon disulfide, alumina-silica pellets (alumina:silica = 90:10 by weight, baked product at 800° C for 3 hours) and methyl mercaptan are used respectively. During the reaction, the resulting product is sampled from time to time and analyzed by gas chromatography. It is found that the conversion of the cyclohexanone dimer achieved is always 100% over the reaction period of 1,200 hours. Table 2 also shows the selectivity for o-phenylphenol.

EXAMPLE 19

The same procedure as in Example 14 is repeated except that in place of 0.1 wt.% of carbon disulfide based on the catalyst, 0.3 wt.% of diethylsulfide based on the catalyst is used.

The same analysis as in Example 14 confirms 100% conversion. Table 2 shows the selectivity for o-phenylphenol.

COMPARISON EXAMPLE 2

The same procedure as in Example 14 is repeated except that carbon disulfide is not used. During the reaction, the resulting product is sampled from time to time and analyzed by gas chromatography. It is found that the conversion of the cyclohexanone dimer achieved is always 100% over the reaction period of 1,200 hours. Table 2 also shows the selectivity for o-phenylphenol.

Table 2

| Reaction period (hr.) | Selectivity for o-phenylphenol (mol %) | | | | | | Comp. Ex- ample 2 |
|---|---|---|---|---|---|---|---|
| | Example | | | | | | |
| | 14 | 15 | 16 | 17 | 18 | 19 | |
| 1 | — | — | — | — | — | — | 58.7 |
| 2 | — | 91.2 | — | — | — | — | — |
| 3 | 94.0 | — | 92.0 | 88.2 | 82.8 | — | 74.6 |
| 4 | — | — | — | — | — | 86.0 | — |
| 5 | 94.1 | 91.3 | 92.1 | — | — | — | — |
| 6 | — | 90.5 | — | 90.0 | 89.6 | 90.5 | 78.3 |
| 8 | — | — | — | — | — | — | 79.6 |
| 10 | 94.2 | 91.2 | 92.1 | — | — | — | — |
| 11 | — | — | — | — | 92.8 | — | 82.8 |
| 12 | — | — | — | 91.3 | — | 95.0 | — |
| 14 | — | — | — | — | 93.4 | — | — |
| 15 | — | 90.8 | — | — | — | — | — |
| 20 | 94.2 | — | 92.2 | — | — | 95.2 | — |
| 50 | — | 90.8 | 92.3 | 92.0 | 93.3 | 95.2 | 84.0 |
| 100 | 94.1 | 90.7 | 91.3 | 92.4 | 93.0 | 95.0 | 85.6 |
| 500 | 93.0 | 89.5 | 91.0 | 92.0 | 92.8 | 94.3 | 85.3 |
| 1200 | 92.2 | 90.0 | 90.5 | 91.2 | 92.0 | 93.0 | 83.8 |
| 2000 | 91.3 | — | 89.1 | 90.0 | 90.8 | 91.5 | — |

What we claim is:

1. A process for preparing o-phenylphenol by dehydrogenating at least one cyclohexanone dimer and o-cyclohexylphenol in the presence of a catalyst wherein the catalyst is prepared by a process which comprises the following steps:
   (a) contacting a metal oxide carrier with an aqueous solution or dispersion of at least one compound capable of producing platinum or palladium on said carrier and containing 0.1 to 3.0% by weight of platinum or palladium based on the weight of the carrier;
   (b) contacting said carrier with an aqueous solution or dispersion of 0.5 to 8.0% by weight, based on the weight of the carrier, of at least one alkali substance capable of producing an alkali metal oxide on said carrier;
   (c) heating the carrier in nitrogen atmosphere at 300° to 400° C;
   (d) heating the carrier in hydrogen atmosphere at a temperature of 300° to 400° C;
   (e) contacting the resulting carrier having platinum or palladium and alkali metal oxide thereon with an aqueous solution or dispersion containing 0.05 to 5% by weight, based on the weight of the platinum or palladium and the alkali substance, of at least one sulfur containing compound selected from the group consisting of hydrogen sulfide, organic sulfur compounds, and alkali metal sulfides;
   (f) heating the resulting carrier at 300° to 400° C; and
   (g) contacting the carrier with a gas of said sulfur containing compound and an inert gas at 300° to 400° C.

2. A process according to claim 1, in which said compound capable of producing an alkali metal oxide on the carrier is at least one member selected from the group consisting of alkali metal hydroxides, alkali metal carbonates, and alkali metal oxides.

3. A process according to claim 2 in which said alkali metal is at least one member selected from the group consisting of sodium or potassium.

4. A process according to claim 1, in which said sulfur containing compound is an organic sulfur compound at least one of carbon disulfide, selected from the group consisting of aliphatic mercaptans, aromatic mercaptans, heterocyclic compounds, monosulfides represented by the formula R—S—R' wherein R and R' may be the same or different and are each aliphatic alkyl or benzyl or phenyl group having or not having alkyl, and disulfides represented by the formula R—S—S—R' wherein R and R' are as defined above.

5. A process according to claim 4, in which said organic sulfur compound is at least one member selected from the group consisting of methyl mercaptan, ethyl mercaptan, lauryl mercaptan, phenyl mercaptan, thiophene, thiophthene, dimethyl sulfide diethyl sulfide, dimethyl disulfide and diethyl disulfide.

6. A process according to claim 1, in which said sulfur containing compound is used in an amount of about 0.05 to about 2.0% by weight, based on the total amount of the platinum and palladium and of the alkali substance.

7. A process according to claim 1, wherein said resulting carrier having platinum or palladium and alkali metal oxide thereon, prior to being contacted with said sulfur containing compound, is contacted with at least one alkali metal salt of a sulfur-oxygen acid and subsequently heated at 300° to 400° C.

8. A process according to claim 7, in which said alkali metal salt of sulfur-oxygen acid is at least one species selected from the group consisting of alkali metal salts and alkali metal hydrogen salts of sulfuric acid, sulfurous acid and thiosulfuric acid.

* * * * *